United States Patent [19]

Knifton

[11] 4,356,332

[45] Oct. 26, 1982

[54] PROCESS FOR PREPARING ETHYLENE GLYCOL

[75] Inventor: John F. Knifton, Austin, Tex.

[73] Assignee: Texaco Inc., White Plains, N.Y.

[21] Appl. No.: 316,197

[22] Filed: Oct. 29, 1981

[51] Int. Cl.³ ............................................. C07C 31/20
[52] U.S. Cl. ................................................... 568/852
[58] Field of Search ......................................... 568/852

[56] References Cited

U.S. PATENT DOCUMENTS 4,144,401 3/1979 Wall ..................................... 568/852
4,200,765 4/1980 Goetz ................................... 568/852

Primary Examiner—Joseph E. Evans
Attorney, Agent, or Firm—Carl G. Ries; Jack H. Park; Walter D. Hunter

[57] ABSTRACT

This invention pertains to the production of ethylene glycol by reaction of formaldehyde with carbon monoxide and hydrogen in the presence of a catalyst comprising a cobalt-containing compound and a tin-or germanium-containing promoter and in the presence of substantially inert, oxygenated hydrocarbon solvent.

19 Claims, No Drawings

PROCESS FOR PREPARING ETHYLENE GLYCOL

BACKGROUND OF THE INVENTION

1. Field of the Invention

This invention relates to a process for the preparation of ethylene glycol by the reaction of synthesis gas and formaldehyde using a specific catalyst system and in the presence of a substantially inert, oxygenated hydrocarbon solvent.

2. Prior Art

Ethylene glycol is an important chemical with many important industrial uses. For example, large quantities of ethylene glycol are used as antifreeze or coolant, as a monomer for polyester production as a solvent and as an intermediate in the production of commercial chemicals etc. In conventional processes, ethylene glycol and the corresponding polyol homologues are generated from ethylene via oxidation of the latter to ethylene oxide followed by hydrolysis. Since the cost of materials derived from petroleum sources has been rising rapidly, research effects are now underway to find new processes for producing ethylene glycol which do not utilize an olefin as the starting material. One of the newer methods of preparing ethylene glycol is by reacting carbon monoxide and hydrogen with formaldehyde. For example, formaldehyde, carbon monoxide and hydrogen can be reacted as described in U.S. Pat. No. 2,451,333 over a cobalt catalyst to produce a mixture of polyhydroxy compounds which includes ethylene glycol, higher polyols, glycerol etc. Ethylene glycol has also been prepared by reaction of synthesis gas and formaldehyde with a cobalt catalyst containing trivalent phosphorus, arsenic and antimony compounds (see Japanese Pat. No. 76-128903). Rhodium or rhodium-containing compounds has also been used for the production of ethylene glycol by reaction of formaldehyde, carbon monoxide and hydrogen. This technology is illustrated in U.S. Pat. No. 4,144,401.

A two-stage process for manufacturing ethylene glycol from formaldehyde, carbon monoxide and hydrogen has been described in U.S. Pat. No. 4,200,765, wherein in the first stage, glycol aldehyde is generated at elevated temperature and superatmospheric pressure in the presence of a rhodium catalyst. Subsequent reduction of the glycol aldehyde intermediate yields ethylene glycol as the substantially exclusive polyol product. Other methods for preparing glycol aldehydes are set forth in U.S. Pat. No. 3,920,753, in German Pat. No. 2,741,589 and in European Patent Application No. 0,002,908.

All of these prior art processes for preparing ethylene glycol and glycol aldehydes suffer from one or more disadvantages. Usually a mixture of wide variety of products is formed thus leading to the necessity of time-consuming separation techniques. In addition, the selectivity of these processes to the desired ethylene glycol in most of the process disclosed is low.

One of the objects of this invention is to provide a novel process for preparing ethylene glycol by means of a unique catalyst system in which the feedstock utilized comprises formaldehyde and synthesis gas.

Another object of this invention is to provide a process for producing ethylene glycol with a high degree of selectively from formaldehyde and synthesis gas under moderate conditions of temperature and pressure.

SUMMARY OF THE INVENTION

In this invention ethylene glycol is prepared by reaction of formaldehye and synthesis gas in the presence of a catalyst comprising a cobalt-containing compound and a tin- or germanium-containing promoter and in the presence of a substantially inert oxygenated hydrocarbon solvent, at superatmospheric pressures. Utilizing this one step process a glycol-rich mixture of ethylene glycol and methanol is formed.

The process of this invention is shown in the following equation:

$$CO + 2H_2 + HCHO \xrightarrow[\text{Solvent}]{\text{Catalyst}} HOCH_2CH_2OH \qquad (1)$$

A high degree of selectivity to ethylene glycol is exhibited by the reaction of this invention. Advantageously, in this process the catalyst is one or more inexpensive cobalt-containing compounds in combination with a tin or germanium promoter. Further, relatively low pressures in the reaction system result in a liquid product consisting essentially of ethylene glycol with methanol as the only major organic by-product.

DETAILED DESCRIPTION OF THE INVENTION

This invention relates to a process for preparing ethylene glycol by a process which comprises reacting a mixture of hydrogen, carbon monoxide and formaldehyde in the presence of a catalyst comprising a cobalt-containing compound and a tin- or germanium-containing promoter at superatmospheric pressures of about 500 psi or greater until substantial formation of the said ethylene glycol has been achieved and recovering the said glycol from the reaction mixture.

In carrying out the reaction of this invention selectively to produce high yields of the desired ethylene glycol it is necessary to supply sufficient carbon monoxide, hydrogen and formaldehyde to at least satisfy the stoichiometry of equation (1) above, although an excess of one or more of the reactants over the stoichiometric amounts may be present.

Catalysts that are suitable for use in the practice of this invention contain cobalt. The cobalt-containing compounds may be chosen from a wide variety of organic or inorganic compounds, complexes, etc., as will be shown and illustrated below. It is only necessary that the catalyst precursor actually employed contain said metal in any of its ionic or complexed states in conjunction with carbon monoxide and hydrogen.

The cobalt-containing catalyst precursors may take many different forms. For instance, the cobalt may be added to the reaction mixture in an oxide form, as in the case of, for example, cobalt(II) oxide (CoO) or cobalt-(II, III) oxide ($Co_3O_4$). Alternatively, it may be added as the salt of a mineral acid, as in the case of cobalt(II) chloride ($CoCl_2$), cobalt(II) chloride hydrate ($CoCl_2.6H_2O$), cobalt(II) bromide ($CoBr_2$), cobalt(II) iodide ($CoI_2$) and cobalt(II) nitrate hydrate ($Co(NO_3)_2.6H_2O$), etc., or as the salt of a suitable organic carboxylic acid, for example, cobalt(II) formate, cobalt(II) acetate, cobalt(II) propionate, cobalt naphthenate, cobalt acetylacetonate, etc. The cobalt compound may also be added to the reaction zone as a carbonyl or hydrocarbonyl derivative or as a compound capable of forming a cobalt carbonyl. Suitable examples of carbonyl and hydrocarbonyl compounds which may be employed under reaction conditions, include dicobalt octacarbonyl (Co$_2$(CO)$_8$), cobalt hydrocarbonyl (HCo(CO)$_4$) and substituted carbonyl species such as the triphenylphosphine cobalt tricarbonyl dimer, etc., Preferred cobalt-containing compounds include oxides of cobalt, cobalt salts of a mineral acid, cobalt salts of organic carboxylic acids and cobalt carbonyl or hydrocarbonyl derivatives. Among these, particularly preferred are cobalt(II) chloride, cobalt acetylacetonate, cobalt(II) acetate, cobalt(II) propionate, and dicobalt octacarbonyl.

The tin-containing promoter compound which may be utilized with the cobalt-containing compounds in this process may also take many different forms. For instance the tin may be added to the reaction mixture in elemental form, or in the form of a halide, such as stannic chloride, stannous iodide, stannic bromide, as a hydrocarbyl tin compound such as tetraphenyltin, tetra-n-butyltin, hexamethylditin, tetramethyltin and dibutyl diphenyltin, as an organic-halide tin compound such as trimethyltin chloride, di-t-butyltin dichloride, dimethyltin dichloride, methyltin trichloride, phenyltin trichloride, triethyltin bromide, trimethyltin bromide and tributyltin bromide, as an organotin hydride such as tributyltin hydride, as an organotin oxide such as dimethyltin oxide and diphenyltin oxide, as a carboxylate such as tin(II) caproate, tributyltin acetate and tri-n-propyltin acetate, or as an oxide such as stannous oxide and stannic oxide.

The preferred tin-containing promoter compounds are the hydrocarbyl tin compounds, organotin hydrides and the organo-halide tin compounds. Among these, particularly preferred are tetraphenyltin, tributyltin chloride and tributyltin hydride.

The germanium-containing compounds which may be utilized with the cobalt-containing compounds in this process may also take many different forms. For instance, the germanium may be added to the reaction mixture in the form of a halide, such as germanium tetrachloride, germanium diiodide and germanium tetrabromide, or as a hydrocarbylgermanium compound such as tetra-n-butylgermane, tetraethylgermane, tetraphenylgermane and tetramethylgermane, or an organohalide germanium compound such as diphenylgermanium chloride, methylgermanium trichloride, phenylgermanium trichloride, tin-n-butylgermanium iodide, triethylgermanium chloride, triethylgermanium iodide, trimethylgermanium chloride, triphenylgermanium bromide and triphenylgermanium chloride, or as an organogermanium hydride, such as triphenylgermanium hydride, or as an organogermanium oxide or carboxylate such as triphenylgermanium acetate, or as a germanium alkoxide such as germanium butoxide, germanium ethoxide and germanium methoxide.

The preferred germanium-containing promoter compounds are the organo-halide germanium compounds, the hydrocarbyl germanium compounds, and the organogermanium hydrides. Among these, particularly preferred are triphenylgermanium bromide, trimethylgermanium bromide, triphenylgermanium hydride, tetraphenylgermane, tetraethylgermane and triethylgermanium chloride.

The cobalt-containing compounds and the tin- or germanium-containing promoter may be added separately to the reaction mixture in the synthesis of the desired ethylene glycol (eq. 1), or they may be added as one or more preformed complexes. The preferred preformed complexes are the trialkyl (tetracarbonylcobalt)tin, trialkyl (tetracarbonylcobalt) germanium and triaryl(tetracarbonylcobalt)germanium complexes. Illustrative examples of such performed complexes are triphenyl(tetracarbonylcobalt)germanium (IV) trimethyl(tetracarbonylcobalt)germanium (IV) and tributyl(tetracarbonylcobalt)tin(IV). These complexes are prepared by standard literature methods such as described by D. J. Patmore and W. A. C. Graham, Inorg. Chem. 5, 981 (1967).

The number of gram moles of the tin- or germanium-containing compound employed in this invention per gram atom of cobalt can be varied widely and is generally in the range of 0.01 to 100 and preferably from 0.1 to 5.

The quantity of cobalt catalyst employed in the instant invention is not critical and may vary over a wide range. In general, the novel process is desirably conducted in the presence of a catalytically effective quantity of one or more of the active cobalt species together with one or more of the tin- or germanium-containing promoters which gives the desired products in reasonable yields. The reaction proceeds when employing as little as about $1 \times 10^{-6}$ weight percent and even lesser amounts of cobalt, basis the total weight of the reaction mixture. The upper concentration is dictated by a variety of factors including the particular promoter utilized, the catalyst cost, partial pressures of carbon monoxide and hydrogen, operating temperature, etc. A cobalt catalyst concentration of from about $1 \times 10^{-5}$ to about 10 weight percent cobalt, based on the total weight of reaction mixture, is generally desirable in the practice of this invention.

In addition to formaldehyde, compounds capable of releasing formaldehyde under reaction conditions such as aldehyde polymers including paraformaldehyde and trioxane may be utilized in the process of this invention. The preferred aldehydes, however, are formaldehyde and a paraformaldehyde.

The solvents useful in the process of this invention are one or more oxygenated hydrocarbons, i.e., a compound composed only of carbon, hydrogen and oxygen and one in which the only oxygen atoms present are in ether groups, ester groups, ketone carbonyl groups or hydroxyl groups of alcohols. Generally, the oxygenated hydrocarbon will contain 3 to 12 carbon atoms and preferably a maximum of 3 oxygen atoms. The solvent must be substantially inert under reaction conditions, and it must be one which has a normal boiling point of at least 40° C. at atmospheric pressure and preferably, the solvent will have a boiling point greater than that of methanol and other oxygen-containing reaction products so that recovery of the solvent by distillation is facilitated.

Preferred ester-type solvents are the aliphatic and acrylic carboxylic acid monoesters as exemplified by butyl acetate, methyl benzoate, isopropyl iso-butyrate, and propyl propionate as well as dimethyl adipate. Useful alcohol-type solvents include monohydric alcohols such as cyclohexanol, 1-hexanol, 2-hexanol, neopentanol, 2-octanol, etc. Suitable ketone-type solvents include, for example, cyclic ketones such as cyclohexanone, and 2-methylcyclohexanone, as well as acyclic ketones such as 2-pentanone, butanone, acetophenone, etc. Ethers which may be utilized as solvents include cyclic, acyclic and heterocyclic materials. Preferred ethers are the heterocyclic ethers as illustrated by 1,4-dioxane and 1,3-dioxane. Other suitable ether solvents include di-n-propyl ether, diethylene glycol dibutyl ether, dibutyl ether, ethyl butyl ether, diphenyl ether, heptyl phenyl ether, anisole, tetrahydrofuran, etc. The most useful solvents of all of the above groups include the ethers as represented by monocyclic, heterocyclic ethers such as 1,4-dioxane, etc.

The temperature range which can usefully be employed in these synthesis is a variable dependent upon other experimental factors, including the choice of the aldehyde, the pressure, and the concentration and choice of particular species of the cobalt-containing compound and the tin- or germanium-containing promoter among other things. The range of operability is from about 50° to about 300° C. when superatmospheric pressures of syngas are employed. A narrower range of about 100° to about 250° C. represents the preferred temperature range.

Superatmospheric pressures of about 500 psi or greater lead to substantial yields of ethylene glycol by the process of this invention. A preferred operating range is from about 1000 psi to about 5000 psi, although pressures above 5000 psi also provide useful yields of the desired ethylene glycol. The pressures referred to here represent the total pressure generated by all the reactants, although they are substantially due to the carbon monoxide and hydrogen fractions in these examples.

The relative amounts of carbon monoxide and hydrogen which may be initially present in the syngas mixture are variable, and these amounts may be varied over a wide range. In general, the mole ratio of $CO:H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether.

In all these synthesis in order to achieve a high degree of selectivity the amount of carbon monoxide, hydrogen, and aldehyde in the reaction mixture should be sufficient to at least satisfy the stoichiometry of eq (1). Excess carbon monoxide and/or hydrogen or any of the reactants over the stoichiometric amounts may be present, if desired.

The novel process of this invention can be conducted in a batch, semi-continous or continuous fashion. The catalyst may be initially introduced into the reaction zone batchwise, or it may be continuously or intermittently introduced into such as zone during the course of the synthesis reaction. Operating conditions can be adjusted to optimize the formation of the desired ethylene glycol, and said material may be recovered by methods well known in the art, such as distillation, fractionation, extraction and the like. A fraction rich in cobalt catalyst components may then be recycled to the reaction zone, if desired, and additional products generated.

The products have been identified in this work by one or more of the following analytical procedures, via, gas-liquid phase chromatography (glc), infrared (ir), polarography, Karl Fischer titration, nuclear magnetic resonance (nmr) and elemental analysis, or a combination of these techniques. Analysis have, for the most part, been by parts in weight; all temperatures are in degrees centigrade and all pressures in pounds per square inch gauge (psig).

The following examples which illustrate various embodiments of the invention are to be considered not limitative.

EXAMPLE I

To a 450 ml glass-lined pressure reactor was charged a mixture of dicobalt octacarbonyl (3.0 mole Co), triphenylgermanium hydride (1.5 mole) and paraformaldehyde (0.1 mole) in 1,4-dioxane (15.0 g). The mixture was flushed with nitrogen, the reactor sealed, flushed with synthesis gas, pressured to 2700 psig with 2:1 molar $H_2/CO$ mixture, and heated to 160° C. with agitation. After four hours, the reactor was allowed to cool, the gas pressure (2375 psig) noted, the excess gas sampled and vented, and the red liquid product (21.7 g) recovered.

Analysis of the liquid product by glc and Karl Fischer titration showed it to contain:
 3.1% ethylene glycol
 1.5% ethylene glycol monomethyl ether
 1.9% methanol
 5.5% water
 80.0% 1,4-dioxane solvent Analysis of the liquid product by atomic absorption showed it to contain >98% of the cobalt originally charged. There is no solid product phase. Typical off-gas samples contained:
 59% hydrogen
 35% carbon monoxide
 3.4% carbon dioxide

EXAMPLES 2–10

Following the general procedure of Example 1, cobalt octacarbonyl and various tin and germanium promoters were employed in Examples 2–10. The results are summarized in Table I which follows.

It may be noted that:

(1) Cobalt octacarbonyl coupled with a variety of tin and germanium promoters are effective catalysts for the low pressure synthesis of ethylene glycol from syngas plus formaldehyde.

(2) Ethylene glycol is the predominant organic fraction in many of these experiments. The glycol-to-methanol ratio is 1.6:1, for example in Example 1.

(3) Typical synthesis are conducted under moderate conditions of temperature and pressure.

(4) Cobalt recovery in solution after CO hydrogenation to glycol is essentially quantitative.

(5) The most effective promoters, in terms of glycol productivity and cobalt recovery in solution, were:
 Triphenylgermanium hydride (Example 1)
 Trimethylgermanium bromide (Example 4)
 Tetraphenylgermane (Example 6)
 Tributyltin hydride (Example 7)

TABLE 1

Ethylene Glycol from Syngas Plus Formaldehyde - I[a]

| Example | Catalyst Composition | Liquid Product Composition (Wt. %) | | | | | | | Cobalt[c] recov. % | Off-gas composition (%) | | |
|---|---|---|---|---|---|---|---|---|---|---|---|---|
| | | $(CH_2OH)_2$ | $CH_2OH$ \| $CH_2OMe$ | $CH_3OH$ | $H_2O$ | p-Dioxane | MeOOCH | HCHO | | $H_2$ | CO | $CO_2$ |
| 1 | $Co_2(CO)_8$—$Ph_3GeH$ | 3.1 | 1.5 | 1.9 | 5.5 | 80.0 | 0.7 | | >98 | 59.2 | 34.8 | 3.4 |
| 2 | $Co_2(CO)_8$—$Et_3GeCl$ | 2.2 | 1.0 | 2.0 | 5.8 | 80.9 | 0.7 | | >98 | 56.1 | 39.6 | 2.3 |
| 3 | $Co_2(CO)_8$—$Ph_3GeBr$ | 2.1 | 0.7 | 2.0 | 5.5 | 82.3 | 0.6 | | 90 | 52.9 | 41.1 | 3.2 |
| 4 | $Co_2(CO)_8$—$Me_3GeBr$ | 3.0 | 1.2 | 1.7 | 6.3 | 80.7 | 0.6 | None | >98 | | | |
| 5 | $Co_2(CO)_8$—$Ph_4Ge$ | 2.7 | 1.3 | 1.5 | 5.9 | 81.5 | 0.4 | 0.5 | >98 | 58.2 | 38.5 | 2.0 |
| 6 | $Co_2(CO)_8$—$Et_4Ge$ | 2.3 | 1.6 | 2.3 | 4.9 | 79.8 | 0.6 | | 97 | 61.8 | 34.7 | 2.0 |
| 7 | $Co_2(CO)_8$—$Bu_3SnH$ | 2.8 | 1.6 | 2.2 | 5.0 | 80.1 | 0.7 | | 84 | 57.5 | 37.0 | 3.6 |
| 8 | $Co_2(CO)_8$—$Bu_3SnCl$ | 1.4 | 0.7 | 2.9 | 5.2 | 84.6 | 0.8 | | 36 | 59.4 | 37.1 | 2.3 |
| 9 | $Co_2(CO)_8$—$Ph_3SnH$ | Trace | 0.1 | 4.0 | 4.9 | 86.0 | 1.4 | 0.03 | 75 | 53.7 | 40.9 | 3.1 |
| 10 | $Co_2(CO)_8$—$Ph_4Sn$ | 1.1 | 0.4 | 2.9 | 5.6 | 83.3 | 0.7 | | 97 | 55.8 | 40.0 | 1.9 |

[a]Reaction charge: Co, 3.0 mmole; Ge/Sn, 1.5 mmole; (HCHO), 0.1 mmole; 1.4 dioxane, 15 gm. Operating conditions: 2700 psig initial pressure (CO/$H_2$, 1:2); 160° C.; 4 hr.
[b]Analysis by: glc (method for ethylene glycol, etc.); Karl Fischer ($H_2O$); polarographic (HCHO).
[c]Cobalt analysis by atomic absorption

EXAMPLES 11-29

Following the general procedure of Example 1, cobalt octacarbonyl coupled with various tin and germanium promoters were evaluated in variety of different ethereal solvents over a range of operating temperatures, pressures, reaction times and at different initial formaldehyde and cobalt concentrations. Also varied were the initial Co/Ge atomic ratios. The results are summarized in Table 2 which follows.

It may be noted that:

(1) In Example 13 the product solution contains 4.6 wt. % ethylene glycol and 1.9 wt. % ethylene glycol monomethyl ether. The total glycol content was estimated thereby to be 6.5 wt. %, the methanol-to-glycol weight ratio was 1:3.3 and cobalt recovery in solution was >98 wt. %.

(2) Glycol formation was observed over a wide range of operating temperatures, pressures and hold times. Conversion of paraformaldehye was essentially complete for these batch runs.

(3) A variety of ethereal solvents, including 1,4-dioxane, diphenyl ether, dipropyl ether, tetrahydrofuran and aqueous 1,4 dioxane, were employed as solvents in this ethylene glycol synthesis.

TABLE 2

Ethylene Glycol from Syngas Plus Formaldehyde - II[a]

| Example | Catalyst Composition | Temp (°C.) | Press (psig) | Time (hr) | Solvent | Coreactant | (CH$_2$OH)$_2$ | CH$_2$OH—CH$_2$OMe | CH$_3$OH | H$_2$O | Solvent/1,4-Dioxane | MeOOCH | HCOH | Cobalt Recovery (%) |
|---|---|---|---|---|---|---|---|---|---|---|---|---|---|---|
| 11 | Co$_2$(CO)$_8$—2Ph$_3$GeH | 160 | 2700 | 4 | 1,4-Dioxane | (HCHO)$_n$ | 2.7 | 2.0 | 3.1 | 4.6 | 80.0 | 0.3 | None | >98 |
| 12 | 2Co$_2$(CO)$_8$—2Ph$_4$Ge | " | " | " | " | " | 4.1 | 1.8 | 1.1 | 6.7 | 77.7 | 0.2 | None | 94 |
| 13 | 4Co$_2$(CO)$_8$—4EtGe | " | " | " | " | " | 4.6 | 1.9 | 1.1 | 7.2 | 70.7 | 0.6 | 0.04 | 48 |
| 14 | Co$_2$(CO)$_8$—Ph$_4$Ge | " | " | " | " | 2(HCHO)$_n$ | 4.3 | 2.1 | 3.0 | 10.6 | 69.7 | 0.6 | 0.04 | >98 |
| 15 | Co$_2$(CO)$_8$—Ph$_4$Ge | " | " | " | " | 3(HCHO)$_n$ | 3.5 | 2.4 | 8.3 | 9.7 | 66.2 | 3.2 | 0.06 | >98 |
| 16 | Co$_2$(CO)$_8$—2Ph$_3$GeH | 190 | " | " | " | (HCHO)$_n$ | 1.5 | 1.6 | 5.3 | 3.6 | 82.2 |  |  |  |
| 17 | Co$_2$(CO)$_8$—Ph$_3$GeH | 190 | " | " | " | " | 2.2 | 1.9 | 3.8 | 3.7 | 81.9 | 1.2 | 0.03 | >98 |
| 18 | Co$_2$(CO)$_8$—Ph$_3$GeH | 130 | " | " | " | " | 2.0 | 0.8 | 1.2 | 6.6 | 84.6 | 0.3 |  | 97 |
| 19 | Co$_2$(CO)$_8$—Ph$_3$GeH | 160 | 4500 | " | " | " | 3.3 | 0.7 | 1.2 | 6.1 | 79.8 | 0.4 |  | >98 |
| 20 | Co$_2$(CO)$_8$—Ph$_3$GeH | " | 1500 | " | " | " | 1.2 | 2.0 | 3.7 | 4.1 | 85.5 | 0.5 | 0.05 | 88 |
| 21 | Co$_2$(CO)$_8$—Ph$_3$GeH | " | 2700 | 1 | " | " | 2.3 | 1.5 | 2.2 | 5.2 | 79.3 | 0.7 | 0.5 | >98 |
| 22 | Co$_2$(CO)$_8$—Ph$_3$GeH | " | " | 18 | " | " | 2.5 | 1.4 | 1.3 | 6.0 | 79.2 | 0.3 |  | >98 |
| 23 | Co$_2$(CO)$_8$—Ph$_3$GeH | " | " | 4 | 1,4-dioxane/H$_2$O | " | 1.2 |  | 2.0 | 18.8 | 60.5 |  |  | >98 |
| 24 | Co$_2$(CO)$_8$—Ph$_3$GeH | " | " | " | Ph$_2$O | " |  |  | 0.8 | 0.1 | 94.7 | 2.0 | None |  |
| 25 | Co$_2$(CO)$_8$—Bu$_3$SnH | " | " | " | " | " |  |  | 4.0 | 3.7 | 81.4 | 2.8 |  |  |
| 26 | Co$_2$(CO)$_8$—Et$_4$Ge | " | " | " | THF | " | 1.2 | 1.1 | 2.0 | 10.3 | 53.4 | 0.1 | None | >98 |
| 27 | Co$_2$(CO)$_8$—Et$_4$Ge | " | " | " | Pr$_2$O | " | 3.3 | 1.9 | 2.0 | 1.0 | 86.3 | 1.4 |  | <1 |
|  |  |  |  |  |  |  | 0.2[d] |  | 13.3 | 58.0 |  | 0.5 |  |  |
|  |  |  |  |  |  |  | 13.2 |  |  |  |  |  |  |  |
| 28 | Co$_2$(CO)$_8$—Ph$_3$GeH | " | " | " | 1,4-dioxane | (HCHO)$_3$ | [12.8 Start |  | 0.1 | 0.5 | 88.4 |  | 9.7[c] | 93 |
| 29 | Co$_2$(CO)$_8$—Ph$_3$GeH | " | " | " | 1,4-dioxane/EG | (HCHO)$_n$ | 13.2 Finish] |  |  | 0.7 | 96.4 |  | 0.5 |  |
|  |  |  |  |  |  |  |  |  | 1.9 | 6.8 | 77.1 | 0.3 |  |  |

[a]Reaction charge: Co, 3.0 mmole; Ge/Sn, 1.5 mmole; (HCHO)$_m$ 0.1 mmole; 1,4-dioxane, 15 gm.
[b]Analysis as per Table 1
[c]Identified by glc as trioxane.
[d]Two phase product

EXAMPLE 30

To a 450 ml glass-lined pressure reactor was charged a mixture of dicobalt octacarbonyl (2.0 mmole Co), triphenylgermane (2.0 mmole) and paraformaldehyde (0.1 mole) in 1,4-dioxane (15.0 g). The mixture was flushed with nitrogen, the reactor sealed, flushed with syngas, pressured to 2700 psig with 2:1 $H_2/CO$, and heated to 160° C. with agitation. After four hours, the reactor was allowed to cool, the gas pressure (2085 psig) noted, the excess gas sampled and vented, and the red liquid product (21.6 g) recovered.

Analysis (glc and Karl Fischer titration) of the liquid product showed it to contain:

2.7 wt % ethylene glycol
2.0 wt % ethylene glycol monomethyl ether
3.1 wt % methanol
4.6 wt % water
80.7 wt % 1,4-dioxane Analysis of the liquid product by atomic absorption shows it to contain >98% of the cobalt originally charged. There was no solid product phase.

The product liquid was then distilled in vacuo and the ethylene glycol recovered as a distillate fraction. The residual cobalt catalyst was returned to the 450 ml glass-lined reactor by washing with 1,4-dioxane (15.0 g). Fresh formaldehyde (0.1 mole) was also added at this stage, the reactor sealed, flushed with synthesis gas, pressured to 2700 psig with $Co/H_2$ (1:2 molar) and heated to 160° C. with agitation for 4 hours. In this manner the synthesis of ethylene glycol was repeated successfully, and the latter recovered from the crude liquid product (23.6 g) by vacuum distillation as outlined above. Analysis of the liquid product showed it to contain:

3.0 wt % ethylene glycol
2.2 wt % ethylene glycol monomethyl ether
3.4 wt % methanol
11.2 wt % water
0.8 wt % methyl formate
68.3 wt % 1,4-dioxane Analysis of the liquid product by atomic absorption showed it to contain >98% of the cobalt originally charged. There was no solid product phase.

EXAMPLE 31

Following the procedures of Example 1, the 450 ml glass-lined pressure reactor was charged with a mixture of triphenyl(tetracarbonylcobalt)germanium(IV) (3.0 mmole) and formaldehyde (0.1 mole) in 1,4-dioxane (15.0 g). The mixture was flushed with nitrogen, the reactor sealed, flushed with synthesis gas, pressured to 2700 psig with 2:1 molar $H_2/CO$ and heated to 160° C. with agitation. After four hours, the reaction was allowed to cool, the gas pressure (2325 psig) noted, the excess gas sampled and vented, and the red amber liquid product (21.3 g) recovered.

Analysis (glc and Karl Fischer titration) of the liquid product showed it to contain:

3.2 wt % ethylene glycol
2.4 wt % ethylene glycol monoethyl ether
2.4 wt % methanol
1.5 wt % methyl formate
5.0 wt % water
79.9 wt % 1,4-dioxane Analysis of the liquid product by atomic absorption shows it to contain 86% of the cobalt originally charged.

EXAMPLE 32-34

Following the procedure of Examples 1 and 31, a series of trialkyl(tetracarbonylcobalt)germanium(IV), trialkyl(tetracarbonylcobalt)tin(IV), and triaryl(tetracarbonylcobalt)tin(IV) complexes (3.0 mmole) were evaluated for the synthesis of ethylene glycol and ethylene glycol monomethyl ether from synthesis gas plus formaldehyde. The results are summarized in Table 3 below.

It may be noted that the preformed cobalt-germanium and cobalt-tin complexes, i.e., the trimethyl(tetracarbonylcobalt)germanium(IV) and tributyl(tetracarbonylcobalt)tin(IV) complexes, are effective catalysts for the desired glycol synthesis (eq. 1).

TABLE 3

Ethylene Glycol from Syngas Plus Formaldehyde[a]

| Example | Catalyst Composition | Liquid Product Composition (Wt. %) | | | | | | Cobalt recov. (%) | Gas Composition (%) | | |
|---|---|---|---|---|---|---|---|---|---|---|---|
| | | $(CH_2OH)_2$ | $CH_2OH$ \| $CH_2Me$ | $CH_3OH$ | $H_2O$ | 1,4-Dioxane | MeOOCH | | $H_2$ | CO | $CO_2$ |
| 31 | $(Ph_3Ge)Co(CO)_4$ | 3.2 | 2.4 | 2.4 | 5.0 | 79.9 | 1.5 | 86 | 53.2 | 41.1 | 3.0 |
| 32 | $(Me_3Ge)Co(CO)_4$ | 2.0 | 1.3 | 2.7 | 5.6 | 83.9 | 1.3 | | 60.9 | 36.0 | 2.2 |
| 33 | $(Bu_3Sn)Co(CO)_4$ | 0.5 | | 0.6 | 2.9 | 94.1 | 0.6 | 3.6 | 56.7 | 38.6 | 3.6 |
| 34 | $(Ph_3Sn)Co(CO)_4$ | | 0.3 | 2.5 | 95.0 | 0.7 | | <1 | 56.6 | 40.7 | 1.2 |

[a]Charge: Co, 3.0 mmole; $(HCHO)_n$, 0.1 mole; 1,4-dioxane, 15 gm. Operating conditions: 2700 psig initial pressure ($CO/H_2$ 1:2 molar); 160° C./4 hr.

What is claimed is:

1. A process for preparing ethylene glycol which comprises reacting a mixture of hydrogen, carbon monoxide and formaldehyde in the presence of a catalyst comprising a cobalt-containing compound and a promoter selected from the group consisting of a tin-containing compound and a germanium-containing compound and in the presence of a substantially inert oxygenated hydrocarbon solvent at superatmospheric pressures of about 500 psi or greater until substantial formation of the said ethylene glycol has been achieved and recovering the said glycol from the reaction mixture.

2. The process of claim 1 wherein the said reaction mixture is heated at a temperature of from about 50° to about 300° C.

3. The process of claim 1 wherein the said reaction mixture is heated at a temperature of about 100° to about 250° C.

4. The process of claim 1 wherein the process is conducted at a pressure of about 1000 psi to about 5000 psi.

5. The process of claim 1 wherein the said cobalt-containing compound is selected from the group consisting of one or more oxides of cobalt, cobalt salts of a mineral acid, cobalt salts of an organic carboxylic acid and cobalt carbonyl or hydrocarbonyl derivatives.

6. The process of claim 1 wherein the said cobalt-containing compound is selected from the group consisting of cobalt oxide, cobalt chloride, cobalt iodide, cobalt nitrate, cobalt sulfate, cobalt acetate, cobalt propionate, cobalt acetylacetonate, and dicobalt octacarbonyl.

7. The process of claim 6 wherein said cobalt-containing compound is cobalt acetate.

8. The process of claim 6 wherein said cobalt-containing compound is dicobalt octacarbonyl.

9. The process of claim 1 wherein the said promoter is a tin-containing compound.

10. The process of claim 9 wherein the said tin-containing compound is selected from the group consisting of tributyltin hydride, tributyltin chloride and tetraphenyltin.

11. The process of claim 1 wherein the said promoter is a germanium-containing compound.

12. The process of claim 11 wherein the said germanium-containing compound is selected from the group consisting of triethylgermanium hydride, triethylgermanium chloride, triphenylgermanium bromide, trimethylgermanium bromide, tetraphenylgermane and tetraethylgermane.

13. The process of claim 1 wherein the said solvent is selected from the group consisting of 1,3-dioxane, 1,4-dioxane, di-n-propyl ether, diphenyl ether and tetrahydrofuran.

14. The process of claim 1 wherein the said cobalt-containing compound is cobalt octacarbonyl, the said promoter is a tin-containing compound and the said solvent is 1,4-dioxane.

15. The process of claim 1 wherein the said cobalt-containing compound is cobalt octacarbonyl, the said promoter is a germanium-containing compound and the said solvent is 1,4-dioxane.

16. The process of claim 1 wherein the said cobalt-containing compound and said tin-containing promoter are employed as a preformed complex.

17. The process of claim 1 wherein the said cobalt-containing compound and said germanium-containing promoter are employed as a preformed complex.

18. The process of claim 16 wherein said preformed complex is tributyl(tetracarbonylcobalt)tin(IV).

19. The process of claim 17 wherein said preformed complex is selected from the group consisting of triphenyl(tetracarbonylcobalt)germanium(IV) and trimethyl(tetracarbonylcobalt)germanium(IV).

* * * * *

UNITED STATES PATENT AND TRADEMARK OFFICE
CERTIFICATE OF CORRECTION

PATENT NO. : 4,356,332
DATED : October 26, 1982
INVENTOR(S) : John Frederick Knifton It is certified that error appears in the above-identified patent and that said Letters Patent are hereby corrected as shown below:

Col. 13, Line 18, "triethylgermanium" should read
--triphenylgermanium--.

Col. 13, line 18, "triethylegermanium" should read
--triethylgermanium--.

Signed and Sealed this

Twenty-sixth Day of July 1983.

[SEAL]

Attest:

GERALD J. MOSSINGHOFF

Attesting Officer

Commissioner of Patents and Trademarks